US010740561B1

(12) United States Patent
Cao et al.

(10) Patent No.: US 10,740,561 B1
(45) Date of Patent: Aug. 11, 2020

(54) IDENTIFYING ENTITIES IN ELECTRONIC MEDICAL RECORDS

(71) Applicant: Alibaba Group Holding Limited, George Town (KY)

(72) Inventors: Shaosheng Cao, Hangzhou (CN); Jun Zhou, Hangzhou (CN)

(73) Assignee: Alibaba Group Holding Limited, George Town, Grand Cayman (KY)

( * ) Notice: Subject to any disclaimer, the term of this patent is extended or adjusted under 35 U.S.C. 154(b) by 0 days.

(21) Appl. No.: 16/670,533

(22) Filed: Oct. 31, 2019

Related U.S. Application Data (63) Continuation of application No. PCT/CN2019/084197, filed on Apr. 25, 2019.

(51) Int. Cl.
  *G06F 17/27* (2006.01)
  *G06F 40/295* (2020.01)
  *G16H 15/00* (2018.01)
  *G06K 9/00* (2006.01)

(52) U.S. Cl.
  CPC ....... *G06F 40/295* (2020.01); *G06K 9/00456* (2013.01); *G16H 15/00* (2018.01); *G06K 2209/011* (2013.01)

(58) Field of Classification Search
  CPC .................................................. G06F 17/02
  USPC ............................................ 704/1, 9, 10, 257
  See application file for complete search history.

(56) References Cited

U.S. PATENT DOCUMENTS

| 2008/0033720 A1 | 2/2008 | Kankar et al. |
| 2015/0066496 A1 | 3/2015 | Deoras et al. |
| 2017/0139899 A1* | 5/2017 | Zhao ..................... G06F 16/313 |

(Continued)

FOREIGN PATENT DOCUMENTS

| CN | 106980608 | 7/2017 |
| CN | 108874174 | 11/2018 |

(Continued)

OTHER PUBLICATIONS

Cao et al. cw2vec: Learning Chinese Word Embeddings with Stroke n-gram Information. The Thirty-Second AAAI Conference on Artificial Intelligence, Feb. 2-7, 2018, New Orleans, LA USA, pp. 5053-5061 (Year: 2018).*

(Continued)

*Primary Examiner* — Jesse S Pullias
(74) *Attorney, Agent, or Firm* — Fish & Richardson P.C.

(57) ABSTRACT

Disclosed herein are methods, systems, and apparatus, including computer programs encoded on computer storage media, for entity prediction. One of the methods includes performing word segmentation on text to be predicted to obtain a plurality of words. For each word of the plurality of words, a determination is made whether the word has a pre-trained word vector. In response to determining that the word has a pre-trained word vector, the pre-trained word vector for the word is obtained. In response to determining that the word does not have a pre-trained word vector, a word vector for the word is determined based on a pre-trained stroke vector. The word vector and the pre-trained stroke vector are trained based on a text sample and a word vector model. An entity associated with the text is predicted by inputting word vectors of the plurality of words into an entity prediction model.

18 Claims, 8 Drawing Sheets

(56) References Cited

U.S. PATENT DOCUMENTS

| | | | |
|---|---|---|---|
| 2018/0025121 A1* | 1/2018 | Fei | G16H 50/50 |
| | | | 705/3 |
| 2018/0210876 A1 | 7/2018 | Cao et al. | |
| 2019/0188295 A1 | 6/2019 | Sirotkovic et al. | |

FOREIGN PATENT DOCUMENTS

| | | |
|---|---|---|
| CN | 108959252 | 12/2018 |
| CN | 109255119 | 1/2019 |
| CN | 109388807 | 2/2019 |
| EP | 3273387 | 1/2018 |

OTHER PUBLICATIONS

Maimaiti et al. "Bidirectional Long Short-Term Memory Network with a Conditional Random Field Layer for Uyghur Part-Of-Speech Tagging". Information 2017, 8, 157, pp. 1-13 (Year: 2017).*

Zhuang et al. "Chinese Language Processing Based on Stroke Representation and Multidimensional Representation". IEEE Access, vol. 6, pp. 41928-41941, Jul. 26, 2018. (Year: 2018).*

Cao et al., "cw2vec: Learning Chinese Word Embeddings with Stroke n-gram Information," The Thirty-Second AAAI Conference on Artificial Intelligence (AAAI-18), Apr. 2018, pp. 5053-5061.

Crosby et al., "BlockChain Technology: Beyond Bitcoin," Sutardja Center for Entrepreneurship & Technology Technica Report, Oct. 16, 2015, 35 pages.

Huang et al., "Bidirectional LSTM-CRF Models for Sequence Tagging," arXiv:1508.01991, Aug. 2015, 10 pages.

Nakamoto, "Bitcoin: A Peer-to-Peer Electronic Cash System," www.bitcoin.org, 2005, 9 pages.

PCT International Search Report and Written Opinion in International Application No. PCT/CN2019/084197, dated Jan. 31, 2020, 6 pages.

Dong et al., "Character-based LSTM-CRF with radical-level features for Chinese named entity recognition," Natural Language Understanding and Intelligent Applications. ICCPOL 2016, NLPCC 2016. Lecture Notes in Computer Science, 2016, vol. 10102, pp. 239-250.

European Extended Search Report in European Patent Application No. 19738258.3, dated May 29, 2020, 10 pages.

Lample et al., "Neural architectures for names entity recognition," Proceedings of the 2016 Conference of the North American Chapter of the Association for Computational Linguistics: Human Technologies, 2016, pp. 260-270.

Yang et al., "A Condtional Random Fields Approach to Clinical Name Entity Recognition," CCKS Tasks, 6 pages.

\* cited by examiner

(Independent Symptom)

1. On February 1, 2008, the patient was admitted at our general clinic for "feces change and discovery of (Anatomical Site)                                                          (Surgery)

colon lumps for 10 days". On February 5, the patient underwent radical resection of sigmoid colon cancer                                                                                             (Anatomical Site)

(with anastomat). Intraoperative exploration found: no abnormities in the abdominal cavity and other                   (Symptom Description) (Anatomical Site)     (Anatomical Site)

organs, a 4 X 4CM lump on the sigmoid colon proximal to the rectum, intraoperative pathology of ulcerative adenocarcinoma with differentiated stage II-III infiltrating the whole layer, no cancer involvement at the                 (Anatomical Site)

incisal edge, 19 paracolic lymph nodes without metastasis. The patient underwent interventional                            (Medicine)  (Medicine)             (Medicine)  (Medicine)

chemotherapy on January 28 (Eloxatin & Tegafur) and February 23 (Eloxatin & Tegafur), respectively.

Now, the patient is readmitted at our hospital for interventional chemotherapy. In the course of disease, the                                   (Independent Symptom)
                               (Stomach: anatomical site)

patient was in good mental state with poor appetite, fair sleep quality, normal urine and bowel movement.

IDENTIFYING ENTITIES IN ELECTRONIC MEDICAL RECORDS

CROSS-REFERENCE TO RELATED APPLICATIONS

This application is a continuation of PCT Application No. PCT/CN2019/084197, filed on Apr. 25, 2019, which is hereby incorporated by reference in its entirety.

TECHNICAL FIELD

This specification relates to identification of entities in medical records.

BACKGROUND

Many medical records have been converted into electronic medical records (EMRs), and electronic medical records of cooperative hospitals are available. Information in traditional paper medical records can be extracted through image character recognition techniques such as optical character recognition (OCR). Conventional OCR techniques can produce errors based on misinterpretations of positions and lengths of strokes or by imperfect penmanship by the author of an original manual document, such as a medical diagnosis.

Traditional medical record analysis is based on the experience of doctors to manually understand and analyze information in the medical records. In some simple cases, preliminary analysis of the medical records can be done using artificial intelligence (AI) technology, automated intelligent operations, or input provided by doctors. For example, the analysis can determine that a term in the medical records such as "rectal" is associated with an anatomical site and a term such as "tumor" is a symptom description. These types of associations applied to a medical diagnosis description in a medical record can be used to identify corresponding entities (for example, a sigmoid colon) and categorize or classify the entities (for example, as anatomical site). Medical entity identification and categorization (or classification) can be part of an entity identification process used on medical record data. However, some medical records can include typical problems with regard to the data, such as the presence of typos (typographical errors), new terms, or unknown words.

It would be desirable to identify associations in languages that are stroke-based, such as Chinese, particularly in cases where conventional OCR techniques produce erroneous results.

SUMMARY

This specification describes technologies for handling and annotating medical records written in stroke-based languages. These technologies generally involve identifying entities associated with terms in a medical record. For example, the technologies described in this specification can be used to identify suggestions for entities contained in electronic medical records (EMRs), such as anatomical terms, medical conditions, medical procedures, medical staff names, provider names, diagnoses, and medication names.

EMRs can be produced initially, for example, by scanning a hardcopy (e.g., handwritten) medical record into an electronic version, which is then converted to a softcopy text version by conventional OCR techniques. In some cases, the EMRs may contain or result from typographical errors (or "typos") that can make entity identification (also known as named-entity recognition (NER)) from the EMRs inaccurate or impossible. To improve on the shortcomings of conventional OCR techniques, algorithms described in this specification can perform entity identification on EMRs that are OCR-produced, such as to create EMRs that are more correct and accurate. In some embodiments, the technologies described in this specification can be incorporated into OCR applications and tools to improve the correctness and accuracy of EMRs.

This specification also provides one or more non-transitory computer-readable storage media coupled to one or more processors and having instructions stored thereon which, when executed by the one or more processors, cause the one or more processors to perform operations in accordance with embodiments of the methods provided herein.

This specification further provides a system for implementing the methods provided herein. The system includes one or more processors, and a computer-readable storage medium coupled to the one or more processors having instructions stored thereon which, when executed by the one or more processors, cause the one or more processors to perform operations in accordance with embodiments of the methods provided herein.

It is appreciated that methods in accordance with this specification may include any combination of the aspects and features described herein. That is, methods in accordance with this specification are not limited to the combinations of aspects and features specifically described herein, but also include any combination of the aspects and features provided.

The details of one or more embodiments of this specification are set forth in the accompanying drawings and the description below. Other features and advantages of this specification will be apparent from the description and drawings, and from the claims.

BRIEF DESCRIPTION OF THE DRAWINGS

FIG. 1 is a block diagram showing an example of a training process for identifying and classifying terms in accordance with embodiments of this specification.

DETAILED DESCRIPTION

Techniques of the present disclosure can be used to automatically scan electronic medical records written in a stroke-based language, such as Chinese, and efficiently generate suggestions regarding an entity to which a term in a medical record belongs. During the process of suggesting entities, new vocabulary words based on words of the stroke-based language can be added to a vocabulary, which can improve the accuracy of the process of subsequent suggestions of entities.

Techniques described in the present disclosure can be used for entity identification and classification of information in electronic medical records. For example, the techniques can be used to identify entities in medical records that contain stroke-based characters or symbols, such as the Chinese language. The techniques can also be used to identify, and suggest corrections for, errors that exist in electronic medical records. The errors can include misspelled or unknown words, for example. Unknown words can be added to a dictionary that also identifies the entity of each unknown word. Words and phrases can be associated with multiple entities in some cases, and a context (for example, a use of the word or phrase in a sentence) can be used to select the entity that applies in each specific case.

In some embodiments, Chinese word vector techniques, such as the cw2vec algorithm, can be used. The techniques can be used to identify and classify embedded Chinese words, such as by exploiting stroke-level information. In some embodiments, the techniques can include the use and analysis of n-strokes, which capture semantic and morphological level information of Chinese words. Qualitative analysis can demonstrate that models based on n-strokes are able to extract semantic information that cannot be captured by existing techniques. Analysis of empirical results that consider word similarity, word analogy, text classification, and named entity recognition tasks can indicate that the techniques are able to outperform conventional approaches. In some cases, conventional approaches may include word-based techniques (for example, word2vec and GloVe), character-enhanced word embedding (CWE) models, component-based joint learning word embedding (JWE) models, and pixel-based glyph-enhanced word embedding (GWE).

In some embodiments, bi-directional long short term memory, conditional random field (BiLSTM-CRF) algorithms can be used. These algorithms can include mature sequence entity recognition algorithms and training processes that use, as inputs, word vectors and sequence and word category labeling information. Outputs of the algorithms can include algorithm model parameters. In prediction processes of the algorithms, when the inputs include a word vector, algorithm model parameters, and a sequence, the outputs can include annotation information of the word. Techniques described in the present disclosure can use a variety of long short-term memory (LSTM) based models for sequence tagging. The models can include models associated with LSTM networks, bidirectional LSTM (BI-LSTM) networks, LSTM with a conditional random field (CRF) layer (LSTM-CRF), and bidirectional LSTM with a CRF layer (BI-LSTM-CRF). In some embodiments, techniques that are used can first apply a bidirectional LSTM-CRF (denoted as BI-LSTM-CRF) model to natural language processing (NLP) benchmark sequence tagging data sets. The BI-LSTM-CRF model can efficiently use past and future input features because of the existence of a bidirectional LSTM component. The BI-LSTM-CRF model can also use sentence-level tag information because of the existence of a CRF layer. The BI-LSTM-CRF model can produce state-of-the-art accuracy on parts of speech (POS), chunking, and named entity recognition (NER) data sets. The techniques can have a smaller dependence on word embedding as compared to other conventional techniques.

Figure 1:
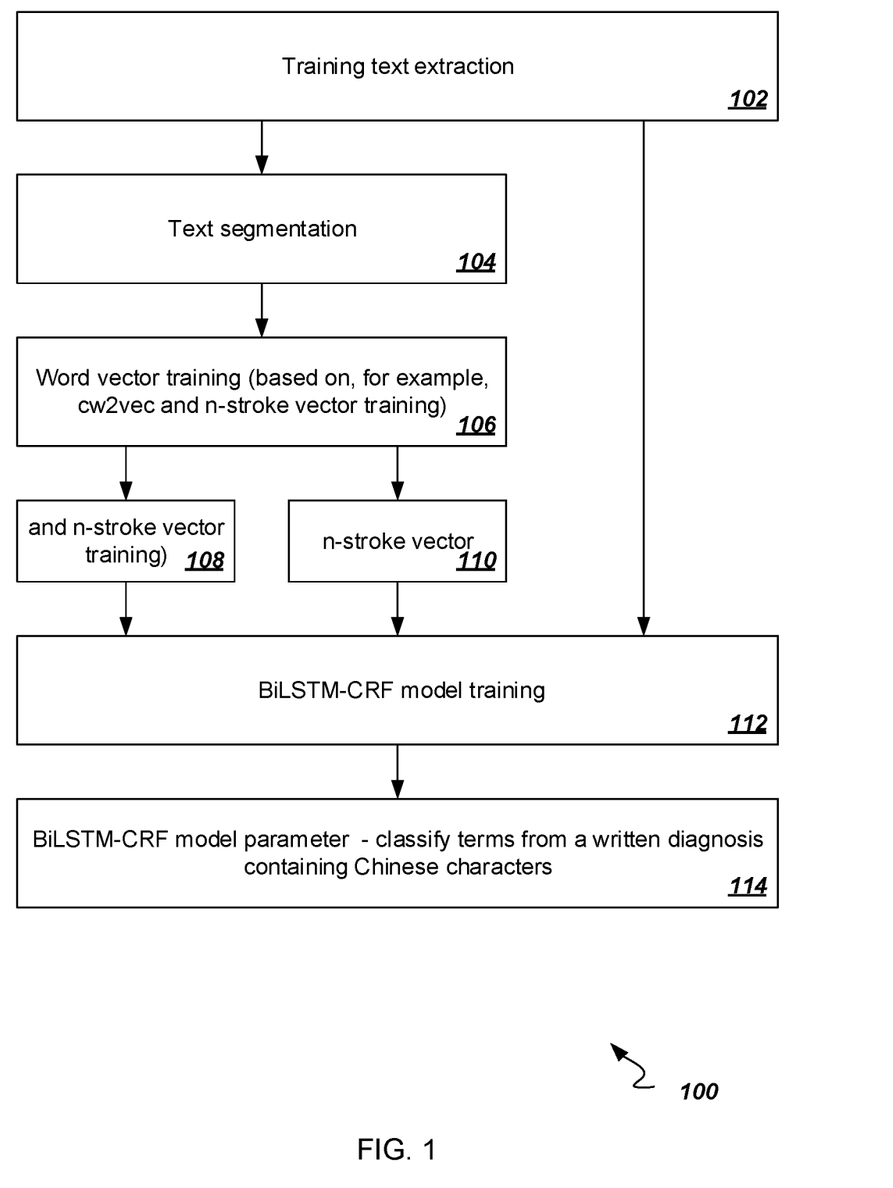
FIG. 1 is a diagram illustrating an example of an environment that can be used to execute embodiments of this specification.
Figure 2:
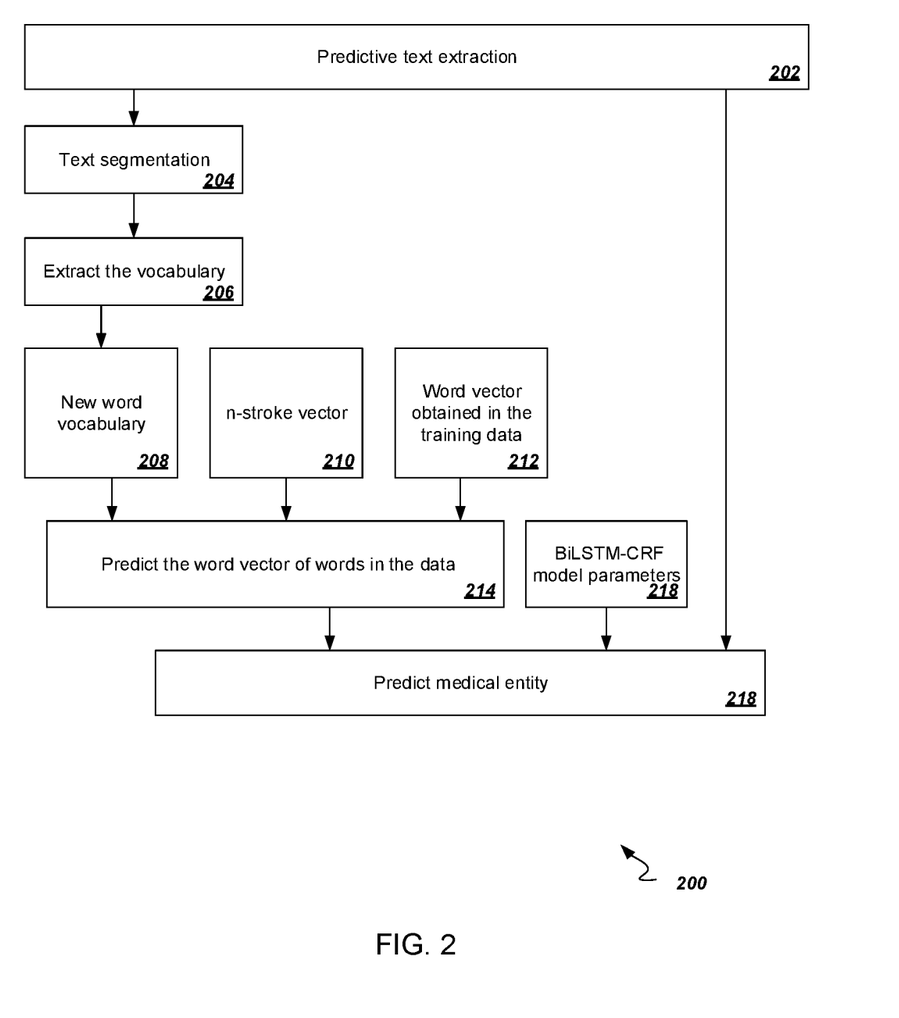
FIG. 2 is a block diagram showing an example of a predictive text extraction process for identifying and classifying terms in accordance with embodiments of this specification.

FIG. 1 is a block diagram showing an example of a training process 100 for identifying and classifying terms in accordance with embodiments of this specification. The training process 100 can create training for entity recognition that can be used to support a forecasting process (FIG. 2).

At 102, training text is extracted from training data. For example, the training data can include an electronic medical record (EMR), and the training text can include medical diagnosis text extracted from EMR.

At 104, text segmentation is performed. As an example, text segmentation can be performed on medical text sentences in the EMR. An example of a medical text sentence is "a radical resection of sigmoid colon cancer was performed (anastomat applied); during the surgery, it is found that abdominal cavity and other organs are not affected; a 4×4 cm lump can be found on sigmoid colon that nears the rectum."

At 106, word vector training is performed. For example, a cw2vec algorithm used for word vector training can be performed on sentences on which word segmentation has occurred. The training can produce a word vector table 108 and an n-stroke vector table 110.

The word vector table 108 can be used for parameter training of a subsequent BiLSTM-CFR model. The n-stroke vector table 110 can be used in prediction processes.

At 112, BiLSTM-CFR model training occurs, for example, to obtain BiLSTM-CFR model parameters. For example, inputs of the training process can include sentences on which training data segmentation has occurred with the word annotation information and trained word vectors. The sentences include annotated or labeled entity information. Outputs of the training process can include the BiLSTM-CFR model parameters.

At 114, BiLSTM-CFR model parameters are stored. The stored BiLSTM-CFR model parameters can be used, for example, to classify terms in a written diagnosis that contains Chinese characters. For example, each word in English can correspond to a character in Chinese that includes strokes. Chinese words can be represented by vectors. The stored BiLSTM-CFR model parameters can be used, for example, in subsequent prediction processes (FIG. 2).

FIG. 2 is a block diagram showing an example of a predictive text extraction process 200 for identifying and classifying terms in accordance with embodiments of this specification. For example, the predictive text extraction process 200 can be used after the training process 100 has been executed. In some embodiments, results of the predictive text extraction process 200 can be used to improve the training process 100, such as iteratively or in a feedback loop.

At 202, prediction text is extracted. For example, prediction text can be text from prediction data. As an example, the prediction data can be an electronic medical record (EMR), and the prediction text can be the text in the EMR for entity prediction.

At 204, text segmentation is performed. As an example, text segmentation can be performed on medical text sentences in the EMR. An example of a medical text sentence is "a radical resection of sigmoid colon cancer was performed (anastomat applied); during the surgery, it is found that abdominal cavity and other organs are not affected; a 4×4 cm lump can be found on sigmoid colon that nears the rectum."

At 206, a vocabulary of words (also referred to as a word vocabulary) are extracted. For example, after the text segmentation has occurred, a vocabulary of words in the EMR can be extracted according to the medical text sentences. In some embodiments, the vocabulary of words can include a new word vocabulary 208, n-stroke vectors 210, and word vectors 212 obtained from the training data. In some embodiments, the new word vocabulary can include one or more words in the EMR that do not exist in the training data. In some embodiments, the n-stroke vectors can be the n-stroke vector obtained according to 110 in the training process 100.

At 214, word vectors are predicted for words (e.g., all words) in the prediction text. For example, for words that have already appeared in the training data, word vectors 212 can be used directly. However, for words that do not appear in the training data (for example, a new word), new words can be calculated from the new word vocabulary 208 and the n-stroke vector 210. In some embodiments, the calculation of new words can include disassembling the word into stroke order, obtaining the n-strokes of the word through the sliding window, and finding the vector of each n-stroke from the n-stroke vector table. The vector can then be used in a vector averaging operation. An averaged vector can be the word vector for the new word.

At 216, the BiLSTM-CRF model parameters are obtained. The parameters can result from obtaining the 112 and 114 in the training process 100.

At 218, a prediction of the medical entity corresponding to the text is made. In some embodiments, inputs of the prediction can include the word vectors and the BiLSTM-CRF model parameters. Outputs of the prediction can include the entity category.

Figure 3A:
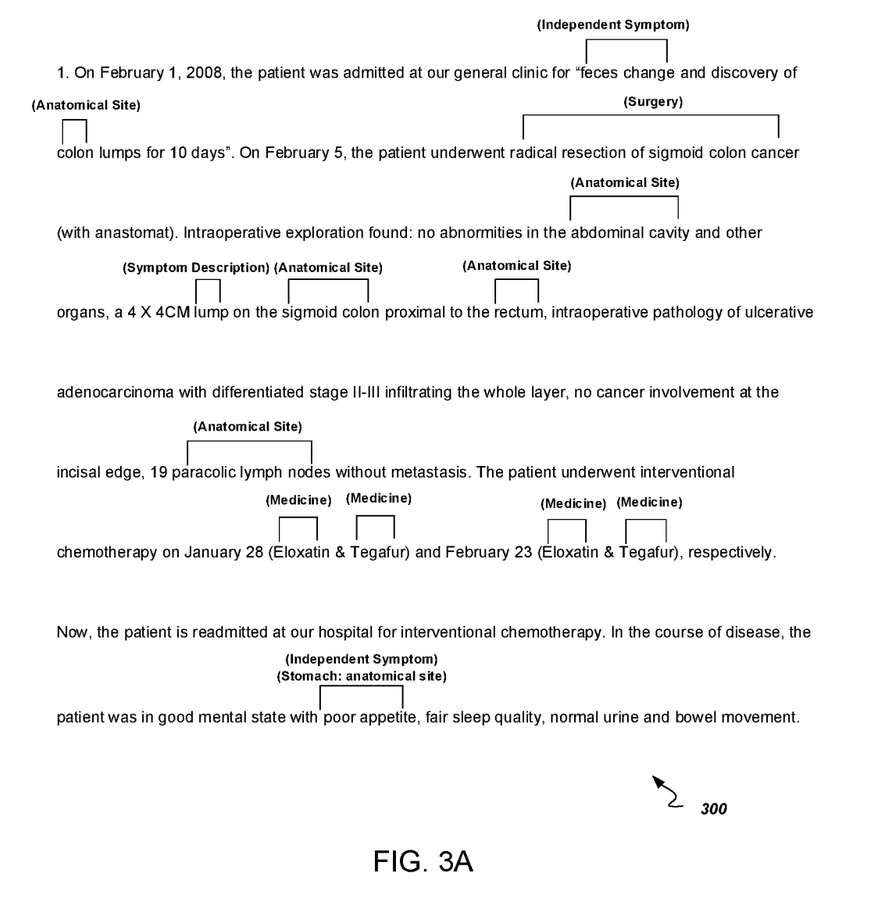
FIGS. 3A and 3B are listings of an example of a medical record case diagram in accordance with embodiments of this specification.
Figure 3B:
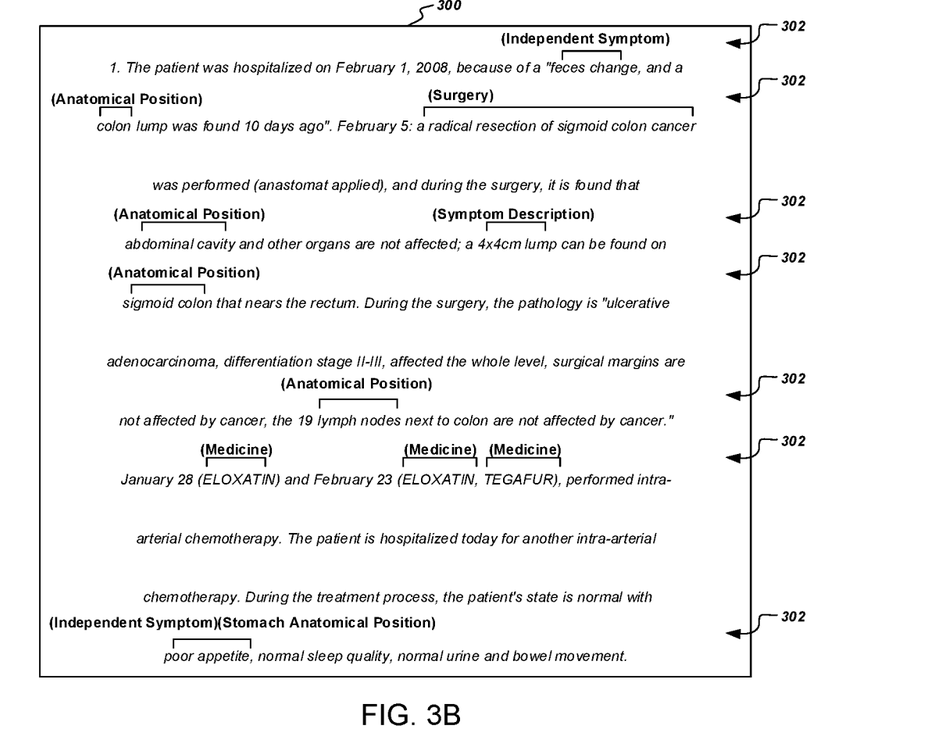

FIGS. 3A and 3B are listings of an example of a medical record case diagram 300 in accordance with embodiments of this specification. FIGS. 3A and 3B show the medical record case diagram 300 in Chinese and English, respectively. Terms in the medical record case diagram 300 are annotated with entities 302 that have been predicted using the predictive text extraction process 200. It can be seen that by using the predictive text extraction process 200, medical entities such as "sigmoid colon," "rectal," and "lumps" can be correctly predicted. Use of techniques described in the present disclosure can solve two major problems. The first problem is to recognize and identify typos (typographical errors) in medical records. For example, the cw2vec algorithm can be used to obtain a certain potential semantic relationship, including recognizing and identifying known entities, through the characterization of n-stroke stroke information. The second problem is new word prediction. For example, using the n-stroke vector table, for words that do not appear in the training data, word vector predictions can be directly performed on the new word so that the information associated with the new word does not go unused or ignored in the EMR.

Figure 4A:
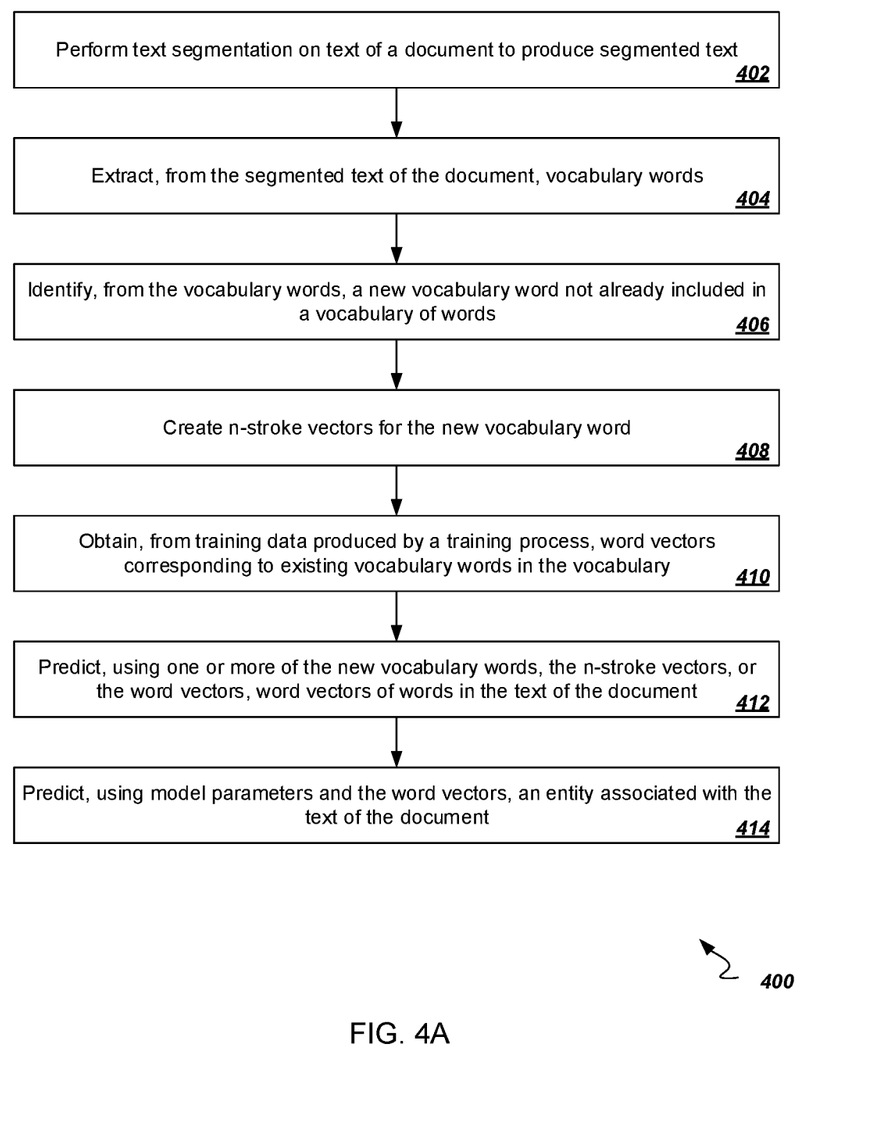
FIG. 4A is a flowchart of an example of a process for predicting entities for new vocabulary words in a document in accordance with embodiments of this specification.

FIG. 4A is a flowchart of an example of a process 400 for predicting entities for new vocabulary words in a document. For convenience, the process 400 will be described as being performed by a system of one or more computers, located in one or more locations, and programmed appropriately in accordance with this specification. For example, an entity prediction system, e.g., a system implementing the process 200 of FIG. 2, appropriately programmed, can perform the process 400.

At 402, text segmentation is performed on text of a document to produce segmented text. As an example, the document can be an EMR written in Chinese, such as the medical record case diagram 300 shown in FIG. 3A. Segmentation of the medical record case diagram 300 can result in a set of words and phrases. From 402, method 400 proceeds to 404.

At 404, vocabulary words are extracted from the segmented text of the document. For example, the extraction from the medical record case diagram 300 can produce a set of medical terms, such as anatomical terms, medical conditions, medical procedures, medical staff names, provider names, diagnoses, and medication names. From 404, method 400 proceeds to 406.

At 406, a new vocabulary word not already included in a vocabulary of words is identified from the vocabulary of words. A new vocabulary of words that is created can include vocabulary words that are EMR-related, for example. As an example, a new vocabulary word not already included in the vocabulary of words can be a new medication or medical procedure not previously identified.

In some embodiments, the vocabulary of words can be created using a training process on a repository of documents. For example, the training process 100 can be used to build a vocabulary of medical terms and corresponding word vectors. From 406, method 400 proceeds to 408.

At 408, n-stroke vectors are created for the new vocabulary word. For example, n-stroke vectors can correspond to Chinese language strokes that are used to create characters in the medical record case diagram 300 shown in FIG. 3A. From 408, method 400 proceeds to 410.

At 410, word vectors corresponding to existing vocabulary words in the vocabulary are obtained from training data produced by a training process. The word vectors can identify existing words that were previously identified, for example. From 410, method 400 proceeds to 412.

At 412, word vectors of words in the text of the document are predicted using one or more of the new vocabulary words, the n-stroke vectors, or the word vectors. For example, individual and groups of strokes can be used to identify the word. The predictions can be based one or mode or the new word vocabulary 208, the n-stroke vectors 210, and the word vectors 212 obtained from the training data. In some embodiments, the word vectors include word vectors of all words in the text of the document. From 412, method 400 proceeds to 414.

At 414, an entity associated with the text of the document is predicted using model parameters and the word vectors. For example, the model parameters can be bi-directional long short term memory, conditional random field (BiLSTM-CRF) model parameters. The entity that is predicted can be an entity from a collection of medically-related entities, for example. After 414, method 400 can stop.

In some embodiments, method 400 can further include annotating the document with entities predicted for words in the document. For example, software that predicts entities associated with words in the medical record case diagram 300 can create the entities 302 that are used to annotate words and phrases in the medical record case diagram 300.

Figure 4B:
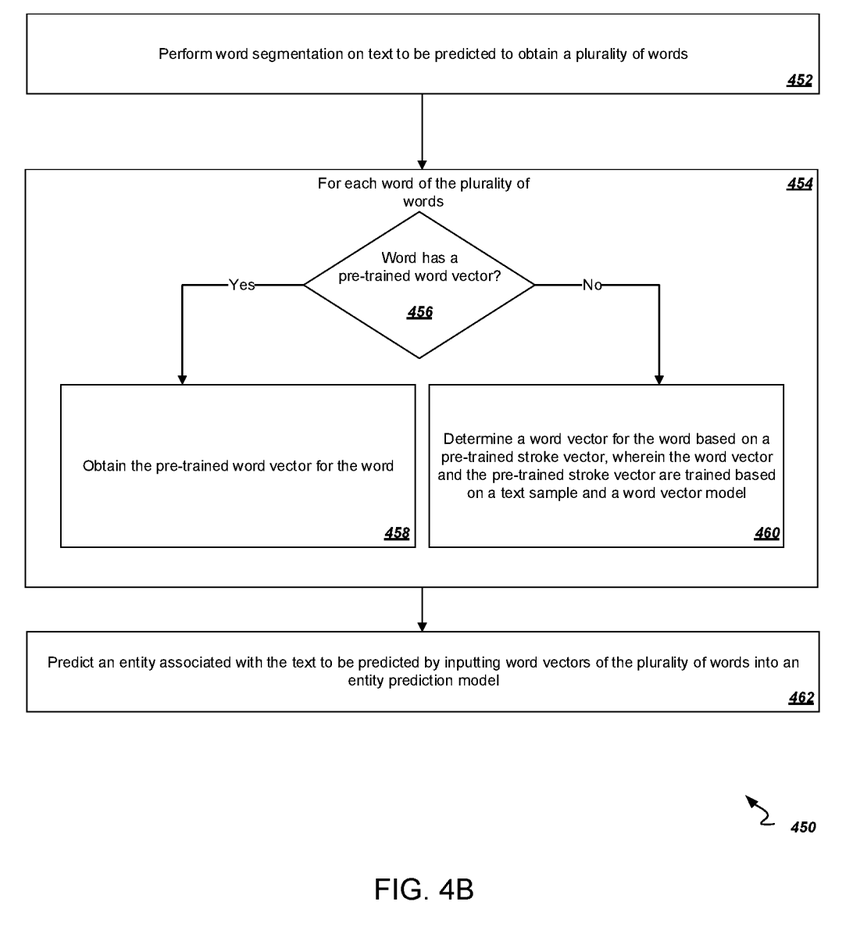
FIG. 4B is a flowchart of an example of a process for predicting entities associated with text.

FIG. 4B is a flowchart of an example of a process 450 for predicting entities associated with text. For convenience, the process 450 will be described as being performed by a system of one or more computers, located in one or more locations, and programmed appropriately in accordance with this specification. For example, an entity prediction system, e.g., a system implementing the process 200 of FIG. 2, appropriately programmed, can perform the process 450.

At 452, word segmentation is performed on text to be predicted to obtain a plurality of words. For example, segmentation can be performed on text in an EMR written in Chinese, such as the medical record case diagram 300 shown in FIG. 3A. The segmentation can result in a set of words and phrases. From 452, method 450 proceeds to 454.

At 454, for each word of the plurality of words, a word vector is determined for the word. As an example, the word segmentation of the text in the medical record case diagram 300 can produce a set of medical terms, such as anatomical terms, medical conditions, medical procedures, medical staff names, provider names, diagnoses, and medication names. The medical terms can be used to construct word vectors. From 454, method 450 proceeds to 456.

At 456, a determination is made whether the word has a pre-trained word vector. For example, the word vector determined for the word can be checked for existence in word vectors that have been pre-trained using a model, such as the word vector table 108. From 456, method 450 proceeds to 458.

At 458, in response to determining that the word has a pre-trained word vector, the pre-trained word vector for the word is obtained. As an example, if it is determined that the word vector already exists in the word vector table 108, then the pre-trained word vector for the word can be obtained from the word vector table 108. From 458, method 450 proceeds to 460.

At 460, in response to determining that the word does not have a pre-trained word vector, a word vector is determined for the word based on a pre-trained stroke vector, wherein the word vector and the pre-trained stroke vector are trained based on a text sample and a word vector model. As an example, if the pre-trained word vector corresponding to the word does not exist in the word vector table 108, then the word vector can be determined from the n-stroke vector table 110.

In some implementations, the text sample can include a medical record text sample, the text to be predicted comprises a medical record text, and the entity comprises a medically-related entity. As an example, the medically-related entity comprises one or more of an anatomical term, a medical condition, a medical procedure, a medical staff name, a provider name, a diagnose, and a medication name.

In some implementations, the text can include a plurality of Chinese characters, and the pre-trained stroke vector can include an n-stroke vector corresponding to Chinese language strokes. In some implementations, the word vector model can be a cw2vec model. For example, the entity prediction model can be a BiLSTM-CRF model. From 460, method 450 proceeds to 462.

At 462, an entity associated with the text to be predicted is predicted by inputting word vectors of the plurality of words into an entity prediction model. For example, a medical entity corresponding to the text can be predicted from an entity model using word vectors and the BiLSTM-CRF model parameters. After 462, method 450 can stop.

Figure 5:
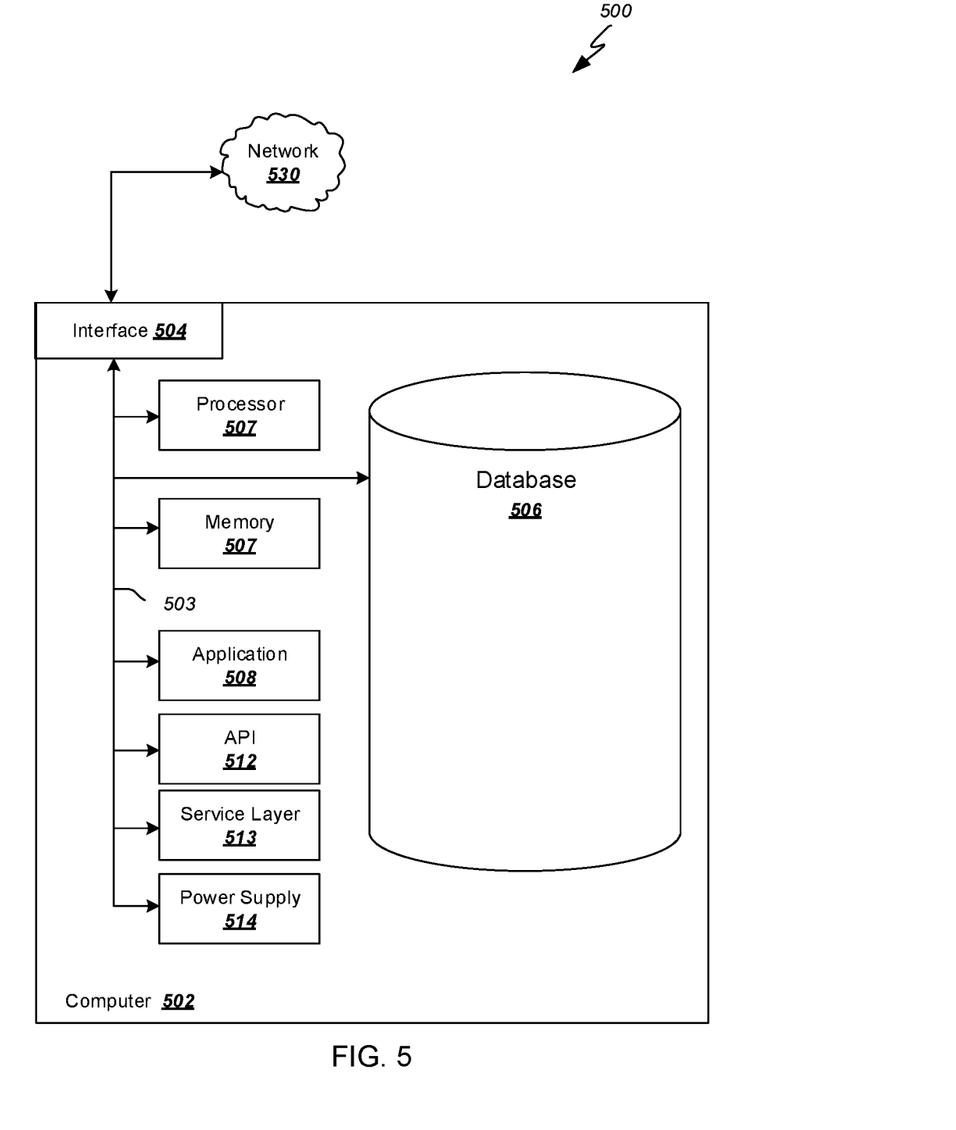
FIG. 5 depicts a block diagram illustrating an example of a computer-implemented system used to provide computational functionalities associated with described algorithms, methods, functions, processes, flows, and procedures in accordance with embodiments of this specification.

FIG. 5 is a block diagram illustrating an example of a computer-implemented System 500 used to provide computational functionalities associated with described algorithms, methods, functions, processes, flows, and procedures, according to an embodiment of the present disclosure. In the illustrated embodiment, System 500 includes a Computer 502 and a Network 530.

The illustrated Computer 502 is intended to encompass any computing device such as a server, desktop computer, laptop/notebook computer, wireless data port, smart phone, personal data assistant (PDA), tablet computer, one or more processors within these devices, another computing device, or a combination of computing devices, including physical or virtual instances of the computing device, or a combination of physical or virtual instances of the computing device. Additionally, the Computer 502 can include an input device, such as a keypad, keyboard, touch screen, another input device, or a combination of input devices that can accept user information, and an output device that conveys information associated with the operation of the Computer 502, including digital data, visual, audio, another type of information, or a combination of types of information, on a graphical-type user interface (UI) (or GUI) or other UI.

The Computer 502 can serve in a role in a distributed computing system as a client, network component, a server, a database or another persistency, another role, or a combination of roles for performing the subject matter described in the present disclosure. The illustrated Computer 502 is communicably coupled with a Network 530. In some embodiments, one or more components of the Computer 502 can be configured to operate within an environment, including cloud-computing-based, local, global, another environment, or a combination of environments.

At a high level, the Computer 502 is an electronic computing device operable to receive, transmit, process, store, or manage data and information associated with the described subject matter. According to some embodiments, the Computer 502 can also include or be communicably coupled with a server, including an application server, e-mail server, web server, caching server, streaming data server, another server, or a combination of servers.

The Computer 502 can receive requests over Network 530 (for example, from a client software application executing on another Computer 502) and respond to the received requests by processing the received requests using a software application or a combination of software applications. In addition, requests can also be sent to the Computer 502 from internal users (for example, from a command console or by another internal access method), external or third-parties, or other entities, individuals, systems, or computers.

Each of the components of the Computer 502 can communicate using a System Bus 503. In some embodiments, any or all of the components of the Computer 502, including hardware, software, or a combination of hardware and software, can interface over the System Bus 503 using an application programming interface (API) 512, a Service Layer 513, or a combination of the API 512 and Service Layer 513. The API 512 can include specifications for routines, data structures, and object classes. The API 512 can be either computer-language independent or dependent and refer to a complete interface, a single function, or even a set of APIs. The Service Layer 513 provides software services to the Computer 502 or other components (whether illustrated or not) that are communicably coupled to the Computer 502. The functionality of the Computer 502 can be accessible for all service consumers using the Service Layer 513. Software services, such as those provided by the Service Layer 513, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the Computer 502, alternative embodiments can illustrate the API 512 or the Service Layer 513 as stand-alone components in relation to other components of the Computer 502 or other components (whether illustrated or not) that are communicably coupled to the Computer 502. Moreover, any or all parts of the API 512 or the Service Layer 513 can be implemented as a child or a sub-module of another software module, enterprise application, or hardware module without departing from the scope of the present disclosure.

The Computer 502 includes an Interface 504. Although illustrated as a single Interface 504, two or more Interfaces 504 can be used according to particular needs, desires, or particular embodiments of the Computer 502. The Interface 504 is used by the Computer 502 for communicating with another computing system (whether illustrated or not) that is communicatively linked to the Network 530 in a distributed environment. Generally, the Interface 504 is operable to communicate with the Network 530 and includes logic encoded in software, hardware, or a combination of software and hardware. More specifically, the Interface 504 can include software supporting one or more communication protocols associated with communications such that the Network 530 or hardware of Interface 504 is operable to communicate physical signals within and outside of the illustrated Computer 502.

The Computer 502 includes a Processor 505. Although illustrated as a single Processor 505, two or more Processors 505 can be used according to particular needs, desires, or particular embodiments of the Computer 502. Generally, the Processor 505 executes instructions and manipulates data to perform the operations of the Computer 502 and any algorithms, methods, functions, processes, flows, and procedures as described in the present disclosure.

The Computer 502 also includes a Database 506 that can hold data for the Computer 502, another component communicatively linked to the Network 530 (whether illustrated or not), or a combination of the Computer 502 and another component. For example, Database 506 can be an in-memory, conventional, or another type of database storing data consistent with the present disclosure. In some embodiments, Database 506 can be a combination of two or more different database types (for example, a hybrid in-memory and conventional database) according to particular needs, desires, or particular embodiments of the Computer 502 and the described functionality. Although illustrated as a single Database 506, two or more databases of similar or differing types can be used according to particular needs, desires, or particular embodiments of the Computer 502 and the described functionality. While Database 506 is illustrated as an integral component of the Computer 502, in alternative embodiments, Database 506 can be external to the Computer 502.

The Computer 502 also includes a Memory 507 that can hold data for the Computer 502, another component or components communicatively linked to the Network 530 (whether illustrated or not), or a combination of the Computer 502 and another component. Memory 507 can store any data consistent with the present disclosure. In some embodiments, Memory 507 can be a combination of two or more different types of memory (for example, a combination of semiconductor and magnetic storage) according to particular needs, desires, or particular embodiments of the Computer 502 and the described functionality. Although illustrated as a single Memory 507, two or more Memories 507 or similar or differing types can be used according to particular needs, desires, or particular embodiments of the Computer 502 and the described functionality. While Memory 507 is illustrated as an integral component of the Computer 502, in alternative embodiments, Memory 507 can be external to the Computer 502.

The Application 508 is an algorithmic software engine providing functionality according to particular needs, desires, or particular embodiments of the Computer 502, particularly with respect to functionality described in the present disclosure. For example, Application 508 can serve as one or more components, modules, or applications. Further, although illustrated as a single Application 508, the Application 508 can be implemented as multiple Applications 508 on the Computer 502. In addition, although illustrated as integral to the Computer 502, in alternative embodiments, the Application 508 can be external to the Computer 502.

The Computer 502 can also include a Power Supply 514. The Power Supply 514 can include a rechargeable or non-rechargeable battery that can be configured to be either user- or non-user-replaceable. In some embodiments, the Power Supply 514 can include power-conversion or management circuits (including recharging, standby, or another power management functionality). In some embodiments, the Power Supply 514 can include a power plug to allow the Computer 502 to be plugged into a wall socket or another power source to, for example, power the Computer 502 or recharge a rechargeable battery.

There can be any number of Computers 502 associated with, or external to, a computer system containing Computer 502, each Computer 502 communicating over Network 530. Further, the term "client," "user," or other appropriate terminology can be used interchangeably, as appropriate, without departing from the scope of the present disclosure. Moreover, the present disclosure contemplates that many users can use one Computer 502, or that one user can use multiple computers 502.

Figure 6:
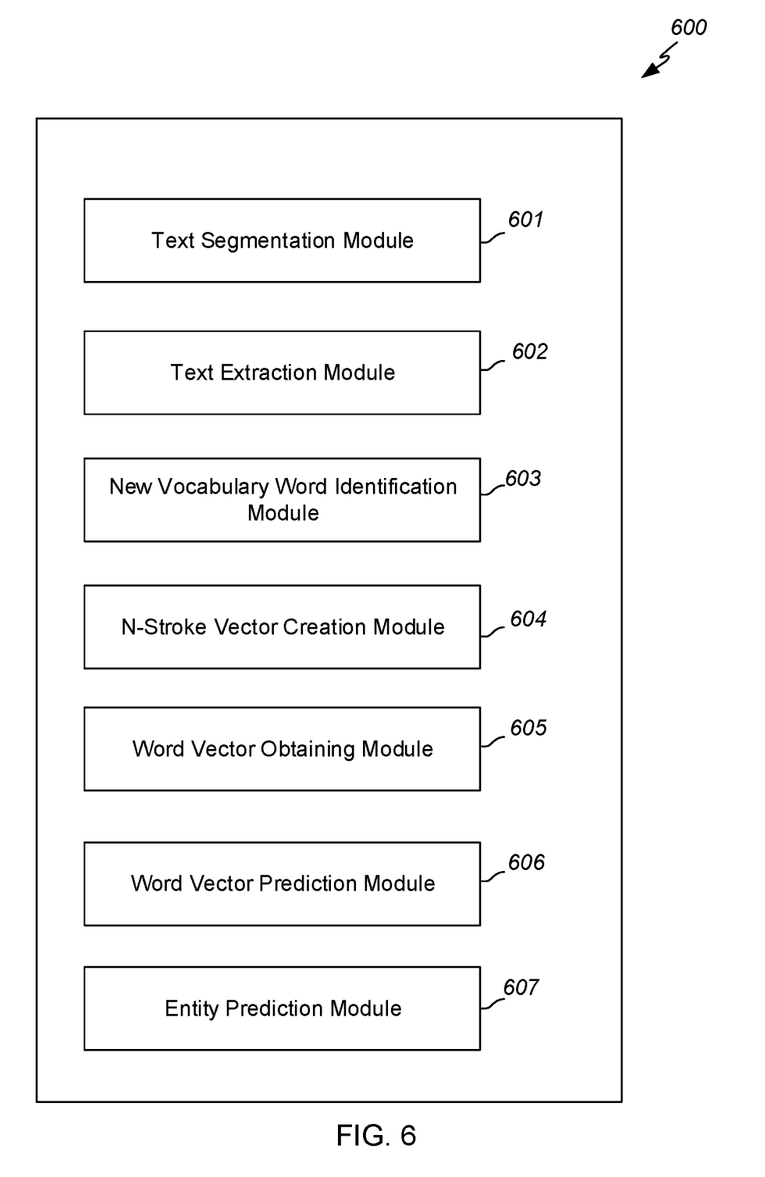
FIG. 6 is a diagram of on example of modules of an apparatus in accordance with embodiments of this specification.

FIG. 6 is a diagram of an example of modules of an apparatus 600 in accordance with embodiments of this specification. The apparatus 600 can correspond to the embodiments described above, and the apparatus 600 includes the following: a text segmentation module 601 for performing text segmentation on text of a document to produce segmented text; a text extraction module 602 for extracting, from the segmented text of the document, vocabulary words; a new vocabulary word identification module 603 for identifying, at least partially based on the vocabulary words, a new vocabulary word not already included in a vocabulary of words; an n-stroke vector creation module 604 for creating n-stroke vectors for the new vocabulary word; a word vector obtaining module 605 for obtaining, from training data produced by a training process, word vectors corresponding to existing vocabulary words in the vocabulary; a word vector prediction module 606 for predicting, using one or more of the new vocabulary words, the n-stroke vectors, or the word vectors, word vectors of words in the text of the document; and an entity prediction module 607 for predicting an entity associated with the text of the document using model parameters and the word vectors.

In an optional embodiment, the apparatus 600 further includes the following: a vocabulary word creation module for creating the vocabulary of words at least partially based on a training process on a repository of documents.

In an optional embodiment of the text segmentation module 601, the document is an electronic medical record (EMR), and wherein the vocabulary is a vocabulary of EMR-related words. In an optional embodiment of the text segmentation module 601, the entities are medically-related entities. In an optional embodiment of the text segmentation module 601, the document is written in Chinese, and wherein the n-stroke vectors correspond to Chinese language strokes. In an optional embodiment of the text segmentation module 601, predicting the word vectors includes performing vector averaging of vectors identified in an n-stroke vector table. In an optional embodiment of the text segmentation module 601, predicting the word vectors includes performing a semantic analysis of typographical errors the document. In an optional embodiment of the text segmentation module 601, the existing vocabulary words in the vocabulary are medical terms including anatomical terms, medical conditions, medical procedures, medical staff names, provider names, diagnoses, and medication names.

In an optional embodiment of the entity prediction module 607, the model parameters are bi-directional long short term memory, conditional random field (BiLSTM-CRF) model parameters.

In an optional embodiment, the apparatus 600 further includes the following: a document annotation module for annotating the document with entities predicted for words in the document.

The system, apparatus, module, or unit illustrated in the previous embodiments can be implemented by using a computer chip or an entity, or can be implemented by using a product having a certain function. A typical embodiment device is a computer, and the computer can be a personal computer, a laptop computer, a cellular phone, a camera phone, a smartphone, a personal digital assistant, a media player, a navigation device, an email receiving and sending device, a game console, a tablet computer, a wearable device, or any combination of these devices.

For an embodiment process of functions and roles of each module in the apparatus, references can be made to an embodiment process of corresponding steps in the previous method. Details are omitted here for simplicity.

Because an apparatus embodiment basically corresponds to a method embodiment, for related parts, references can be made to related descriptions in the method embodiment. The previously described apparatus embodiment is merely an example. The modules described as separate parts may or may not be physically separate, and parts displayed as modules may or may not be physical modules, may be located in one position, or may be distributed on a number of network modules. Some or all of the modules can be selected based on actual demands to achieve the objectives of the solutions of the specification. A person of ordinary skill in the art can understand and implement the embodiments of the present application without creative efforts.

Referring again to FIG. 6, it can be interpreted as illustrating an internal functional module and a structure method for predicting entities in medical records. An execution body in essence can be an electronic device, and the electronic device includes the following: one or more processors; and a memory configured to store an executable instruction of the one or more processors.

The one or more processors are configured to perform text segmentation on text of a document to produce segmented text; extract, from the segmented text of the document, vocabulary words; identify, at least partially based on the vocabulary words, a new vocabulary word not already included in a vocabulary of words; create n-stroke vectors for the new vocabulary word; obtain, from training data produced by a training process, word vectors corresponding to existing vocabulary words in the vocabulary; predict, using one or more of the new vocabulary words, the n-stroke vectors, or the word vectors, word vectors of words in the text of the document; and predict an entity associated with the text of the document using model parameters and the word vectors.

The techniques described in this specification produce one or more technical effects. For example and in some embodiments, techniques of the present disclosure can be used to automatically scan electronic medical records written in a stroke-based language, such as Chinese, and efficiently generate suggestions regarding an entity to which a term in a medical record belongs. During the process of suggesting entities, new vocabulary words based on words of the stroke-based language can be added to a vocabulary, which can improve the accuracy of the process of subsequent suggestions of entities.

Described embodiments of the subject matter can include one or more features, alone or in combination.

For example, in a first embodiment, methods are used for entity prediction. One of the methods includes: performing word segmentation on text to be predicted to obtain a plurality of words; for each word of the plurality of words, determining whether the word has a pre-trained word vector; in response to determining that the word has a pre-trained word vector, obtaining the pre-trained word vector for the word; and in response to determining that the word does not have a pre-trained word vector, determining a word vector for the word based on a pre-trained stroke vector, wherein the word vector and the pre-trained stroke vector are trained based on a text sample and a word vector model, and predicting an entity associated with the text to be predicted by inputting word vectors of the plurality of words into an entity prediction model.

The foregoing and other described embodiments can each, optionally, include one or more of the following features:

A first feature, combinable with any of the following features, specifies that the word vector model comprises a cw2vec model.

A second feature, combinable with any of the previous or following features, specifies that the entity prediction model comprises a bi-directional long short term memory, conditional random field (BiLSTM-CRF) model.

A third feature, combinable with any of the previous or following features, specifies that the text comprises a plurality of Chinese characters, and wherein the pre-trained stroke vector comprises an n-stroke vector corresponding to Chinese language strokes.

A fourth feature, combinable with any of the previous or following features, specifies that the text sample comprises a medical record text sample, the text to be predicted comprises a medical record text, and the entity comprises a medically-related entity.

A fifth feature, combinable with any of the previous or following features, specifies that the medically-related entity comprises one or more of an anatomical term, a medical condition, a medical procedure, a medical staff name, a provider name, a diagnose, and a medication name.

Embodiments of the subject matter and the actions and operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, e.g., one or more modules of computer program instructions, encoded on a computer program carrier, for execution by, or to control the operation of, data processing apparatus. For example, a computer program carrier can include one or more computer-readable storage media that have instructions encoded or stored thereon. The carrier may be a tangible non-transitory computer-readable medium, such as a magnetic, magneto optical, or optical disk, a solid state drive, a random access memory (RAM), a read-only memory (ROM), or other types of media. Alternatively, or in addition, the carrier may be an artificially generated propagated signal, e.g., a machine-generated electrical, optical, or electromagnetic signal that is generated to encode information for transmission to suitable receiver apparatus for execution by a data processing apparatus. The computer storage medium can be or be part of a machine-readable storage device, a machine-readable storage substrate, a random or serial access memory device, or a combination of one or more of them. A computer storage medium is not a propagated signal.

A computer program, which may also be referred to or described as a program, software, a software application, an app, a module, a software module, an engine, a script, or code, can be written in any form of programming language, including compiled or interpreted languages, or declarative or procedural languages; and it can be deployed in any form, including as a stand-alone program or as a module, component, engine, subroutine, or other unit suitable for executing in a computing environment, which environment may include one or more computers interconnected by a data communication network in one or more locations.

A computer program may, but need not, correspond to a file in a file system. A computer program can be stored in a portion of a file that holds other programs or data, e.g., one or more scripts stored in a markup language document, in a single file dedicated to the program in question, or in multiple coordinated files, e.g., files that store one or more modules, sub programs, or portions of code.

Processors for execution of a computer program include, by way of example, both general- and special-purpose microprocessors, and any one or more processors of any kind of digital computer. Generally, a processor will receive the instructions of the computer program for execution as well as data from a non-transitory computer-readable medium coupled to the processor.

The term "data processing apparatus" encompasses all kinds of apparatuses, devices, and machines for processing data, including by way of example a programmable processor, a computer, or multiple processors or computers. Data processing apparatus can include special-purpose logic circuitry, e.g., an FPGA (field programmable gate array), an ASIC (application specific integrated circuit), or a GPU (graphics processing unit). The apparatus can also include, in addition to hardware, code that creates an execution environment for computer programs, e.g., code that constitutes processor firmware, a protocol stack, a database management system, an operating system, or a combination of one or more of them.

The processes and logic flows described in this specification can be performed by one or more computers or processors executing one or more computer programs to perform operations by operating on input data and generating output. The processes and logic flows can also be performed by special-purpose logic circuitry, e.g., an FPGA, an ASIC, or a GPU, or by a combination of special-purpose logic circuitry and one or more programmed computers.

Computers suitable for the execution of a computer program can be based on general or special-purpose microprocessors or both, or any other kind of central processing unit. Generally, a central processing unit will receive instructions and data from a read only memory or a random access memory or both. Elements of a computer can include a central processing unit for executing instructions and one or more memory devices for storing instructions and data. The central processing unit and the memory can be supplemented by, or incorporated in, special-purpose logic circuitry.

Generally, a computer will also include, or be operatively coupled to receive data from or transfer data to one or more storage devices. The storage devices can be, for example, magnetic, magneto optical, or optical disks, solid state drives, or any other type of non-transitory, computer-readable media. However, a computer need not have such devices. Thus, a computer may be coupled to one or more storage devices, such as, one or more memories, that are local and/or remote. For example, a computer can include one or more local memories that are integral components of the computer, or the computer can be coupled to one or more remote memories that are in a cloud network. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Components can be "coupled to" each other by being commutatively such as electrically or optically connected to one another, either directly or via one or more intermediate components. Components can also be "coupled to" each other if one of the components is integrated into the other. For example, a storage component that is integrated into a processor (e.g., an L2 cache component) is "coupled to" the processor.

To provide for interaction with a user, embodiments of the subject matter described in this specification can be implemented on, or configured to communicate with, a computer having a display device, e.g., a LCD (liquid crystal display) monitor, for displaying information to the user, and an input device by which the user can provide input to the computer, e.g., a keyboard and a pointing device, e.g., a mouse, a trackball or touchpad. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser, or by interacting with an app running on a user device, e.g., a smartphone or electronic tablet. Also, a computer can interact with a user by sending text messages or other forms of message to a personal device, e.g., a smartphone that is running a messaging application, and receiving responsive messages from the user in return.

This specification uses the term "configured to" in connection with systems, apparatus, and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions. For special-purpose logic circuitry to be configured to perform particular operations or actions means that the circuitry has electronic logic that performs the operations or actions.

While this specification contains many specific embodiment details, these should not be construed as limitations on the scope of what is being claimed, which is defined by the claims themselves, but rather as descriptions of features that may be specific to particular embodiments. Certain features that are described in this specification in the context of separate embodiments can also be realized in combination in a single embodiment. Conversely, various features that are described in the context of a single embodiments can also be realized in multiple embodiments separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method for entity prediction, the method comprising:
    segmenting a text written in a stroke-based writing system to obtain a plurality of words in the text;
    for each word of the plurality of words obtained from the text written in a stroke-based writing system,
        determining whether the word is associated with a pre-trained word vector,
        if the word is associated with a pre-trained word vector, obtaining the pre-trained word vector for the word,
        if the word is not associated with a pre-trained word vector,
            disassembling the word into constituent strokes,
            forming a plurality of n-strokes based on the constituent strokes,
            for each n-stroke of the plurality of n-strokes, obtaining a corresponding n-stroke vector from an n-stroke table output by a pre-trained model, and
            based on the plurality of corresponding n-stroke vectors, determining a word vector for the word; and
    predicting an entity associated with the text by inputting word vectors of the plurality of words into an entity prediction model.

2. The computer-implemented method of claim 1, wherein the pre-trained model comprises a cw2vec model.

3. The computer-implemented method of claim 1, wherein the entity prediction model comprises a bi-directional long short term memory, conditional random field (BiLSTM-CRF) model.

4. The computer-implemented method of claim 1, wherein the text comprises a plurality of Chinese characters, and wherein each n-stroke comprises one or more Chinese language strokes.

5. The computer-implemented method of claim 1, wherein the pre-trained model is trained on a medical record text sample, the text comprises a medical record text, and the entity comprises a medically-related entity.

6. The computer-implemented method of claim 5, wherein the medically-related entity comprises one or more of an anatomical term, a medical condition, a medical procedure, a medical staff name, a provider name, a diagnose, and a medication name.

7. A non-transitory, computer-readable storage medium storing one or more instructions executable by a computer system to perform operations comprising:
    segmenting a text written in a stroke-based writing system to obtain a plurality of words in the text;
    for each word of the plurality of words obtained from the text written in a stroke-based writing system,
        determining whether the word is associated with a pre-trained word vector,
        if the word is associated with a pre-trained word vector, obtaining the pre-trained word vector for the word,
        if the word is not associated with a pre-trained word vector,
            disassembling the word into constituent strokes,
            forming a plurality of n-strokes based on the constituent strokes,
            for each n-stroke of the plurality of n-strokes, obtaining a corresponding n-stroke vector from an n-stroke table output by a pre-trained model, and
            based on the plurality of corresponding n-stroke vectors, determining a word vector for the word; and
    predicting an entity associated with the text to be predicted by inputting word vectors of the plurality of words into an entity prediction model.

8. The non-transitory, computer-readable storage medium of claim 7, wherein the pre-trained model comprises a cw2vec model.

9. The non-transitory, computer-readable storage medium of claim 7, wherein the entity prediction model comprises a bi-directional long short term memory, conditional random field (BiLSTM-CRF) model.

10. The non-transitory, computer-readable storage medium of claim 7, wherein the text comprises a plurality of Chinese characters, and wherein each n-stroke comprises one or more Chinese language strokes.

11. The non-transitory, computer-readable storage medium of claim 7, wherein the pre-trained model is trained on a medical record text sample, the text comprises a medical record text, and the entity comprises a medically-related entity.

12. The non-transitory, computer-readable storage medium of claim 11, wherein the medically-related entity comprises one or more of an anatomical term, a medical condition, a medical procedure, a medical staff name, a provider name, a diagnose, and a medication name.

13. A computer-implemented system, comprising:
one or more computers; and
one or more computer memory devices interoperably coupled with the one or more computers and having tangible, non-transitory, machine-readable media storing one or more instructions that, when executed by the one or more computers, perform one or more operations comprising:
segmenting a text written in a stroke-based writing system to obtain a plurality of words in the text;
for each word of the plurality of words obtained from the text written in a stroke-based writing system,
  determining whether the word is associated with a pre-trained word vector, if the word is associated with a pre-trained word vector, obtaining the pre-trained word vector for the word,
  if the word is not associated with a pre-trained word vector,
    disassembling the word into constituent strokes,
    forming a plurality of n-strokes based on the constituent strokes,
    for each n-stroke of the plurality of n-strokes, obtaining a corresponding n-stroke vector from an n-stroke table output by a pre-trained model, and
    based on the plurality of corresponding n-stroke vectors, determining a word vector for the word; and
  predicting an entity associated with the text by inputting word vectors of the plurality of words into an entity prediction model.

14. The system of claim 13, wherein the pre-trained model comprises a cw2vec model.

15. The system of claim 13, wherein the entity prediction model comprises a bi-directional long short term memory, conditional random field (BiLSTM-CRF) model.

16. The system of claim 13, wherein the text comprises a plurality of Chinese characters, and wherein each n-stroke comprises one or more Chinese language strokes.

17. The system of claim 13, wherein the pre-trained model is trained on a medical record text sample, the text comprises a medical record text, and the entity comprises a medically-related entity.

18. The system of claim 17, wherein the medically-related entity comprises one or more of an anatomical term, a medical condition, a medical procedure, a medical staff name, a provider name, a diagnose, and a medication name.

* * * * *

UNITED STATES PATENT AND TRADEMARK OFFICE
CERTIFICATE OF CORRECTION

PATENT NO. : 10,740,561 B1
APPLICATION NO. : 16/670533
DATED : August 11, 2020
INVENTOR(S) : Shaosheng Cao and Jun Zhou Page 1 of 1

It is certified that error appears in the above-identified patent and that said Letters Patent is hereby corrected as shown below:

In the Claims

Claim 7, Column 16, Lines 44-45, after "text" delete "to be predicted".

Signed and Sealed this
Sixth Day of October, 2020

Andrei Iancu
*Director of the United States Patent and Trademark Office*